United States Patent [19]

Huber

[11] Patent Number: 4,773,755

[45] Date of Patent: Sep. 27, 1988

[54] METHOD AND APPARATUS FOR DETERMINING THE ZERO LINE IN ATOMIC ABSORPTION SPECTROMETERS

[75] Inventor: Bernhard Huber, Überlingen, Fed. Rep. of Germany

[73] Assignee: Bodenseewerk Perkin-Elmer & Co., GmbH, Überlingen, Fed. Rep. of Germany

[21] Appl. No.: 900,667

[22] Filed: Aug. 27, 1986

[30] Foreign Application Priority Data

Sep. 2, 1985 [DE] Fed. Rep. of Germany ....... 3531276

[51] Int. Cl.$^4$ ............................................. G01N 21/72
[52] U.S. Cl. ..................................... 356/307; 356/315
[58] Field of Search ................. 356/36, 307, 311, 315, 356/417

[56] References Cited

U.S. PATENT DOCUMENTS

| | | | |
|---|---|---|---|
| 3,141,741 | 7/1964 | Hoel et al. | 356/315 X |
| 3,620,628 | 11/1971 | Yasuda et al. | 356/315 X |
| 3,625,614 | 12/1971 | Herrmann et al. | 356/311 |
| 3,681,577 | 8/1972 | Gasiunas | 356/307 X |
| 4,220,413 | 9/1980 | Targowski et al. | 356/315 |
| 4,314,764 | 2/1982 | Liddell et al. | 356/417 X |

FOREIGN PATENT DOCUMENTS 2845426 9/1979 Fed. Rep. of Germany .
2833553 11/1979 Fed. Rep. of Germany .

OTHER PUBLICATIONS

Fresenious Z, Anal. Chem., vol. 315, 1983, pp. 12-19, 1983.
Optik, vol. 19, copy 8, 1962, pp. 422-433, 1962.

*Primary Examiner*—Vincent P. McGraw
*Attorney, Agent, or Firm*—Francis L. Masselle; Ronald G. Cummings; Edwin T. Grimes

[57] ABSTRACT

An apparatus and method for determining the zero line in atomic absorption spectrometers having an atomizer and a burner for atomizing the sample wherein the flow of oxidizing agent supplied to the atomizer is interrupted by means of a switching valve and an additional flow of oxidizing agent is supplied to the burner through a by-pass conduit by-passing the atomizer with the additional flow being equal to the flow of oxidizing agent to the atomizer during operation of the atomizer and the absorption of the measuring light beam defining the zero line.

7 Claims, 2 Drawing Sheets

METHOD AND APPARATUS FOR DETERMINING THE ZERO LINE IN ATOMIC ABSORPTION SPECTROMETERS

BACKGROUND AND SUMMARY OF THE INVENTION

This invention relates generally to atomic absorption spectrophotometers and more particularly to a method and apparatus for determining the zero line in atomic absorption spectrometers of the type which utilize an atomizer and a burner for atomizing the sample.

In an atomic absorption spectrometer, a light source, such as a hollow cathode lamp, is utilized which emits a measuring light beam containing the resonance spectral lines of a desired element. This measuring light beam is passed through a flame burning on a burner and impinges upon a photoelectric detector. The flame is supplied with a fuel gas, e.g. acetylene, and an oxidizing agent, e.g. air or laughing gas. A pneumatic atomizer at the burner is also supplied with oxidizing agent. The atomizer takes in a sample liquid which is entrained by the flow of oxidizing agent and at least partially enters the flame in the form of a fine aerosol. In the flame, the sample liquid is atomized such that the elements contained in the sample form a "cloud of atoms" through which the measuring light beam is passed. The atoms of the looked-for element have a resonance spectrum conforming with the spectral lines of the measuring light beam and absorb the light of the measuring light beam. The attenuation of the measuring light beam is a measure of the amount of the looked-for element in the flame and thus the concentration of the looked-for element in the sample.

The signal obtained at the photoelectric detector of the spectrophotometer must be calibrated or corrected relative to a zero line which is obtained if the sample does not contain the desired element. This zero line can be subjected to drift, for example, due to the fact that the light intensity of the light source changes or the sensitivity of the photoelectric detector changes. It is known from European Patent Publication No. 084,391 to provide a reference path of rays which by-passes the flame so that the radiation by-passing the flame provides a signal at the photoelectric detector which varies only with the drift caused by changes in the light intensity of the light source and by changes in the sensitivity of the detector. This signal can be used to compensate the drift of the signals obtained via the sample path of rays through the flame. During the sample measurement, the radiation continuously passes through the sample path of rays. Between sample measurements, the radiation is passed through the reference path of rays. Movable mirrors are utilized to switch the radiation over from one path of rays to the other upon an external command. The reference measurement is preferably made in the reference path of rays while the flame stabilizes after a change-over from one sample to the other. The measurements in the reference path of rays are stored for use in the drift correction.

This known atomic absorption spectrometer needs complex optical and mechanical means for generating a reference path of rays and for periodic switching between the sample and reference path of rays. Also, the influence of the flame itself upon the zero line is not accounted for. The influence of background absorption is eliminated by an additional measurement using a lamp which emits a continuum, e.g. a deuterium lamp.

It is an object of the present invention to provide a new and improved atomic absorption spectrophotometer device.

Another object of the invention is to provide a new and improved apparatus and method for determining the zero line reference measurement in an atomic absorption spectrophotometer.

A further object of the invention is to provide such an apparatus and method which determines the zero line reference without using a separate reference light path and the precision optical assembly for providing such a reference light path.

A further object of the invention is to provide an apparatus and method for determining the zero line reference which accounts for the effects of the flame upon the zero line measurement.

Another object of the invention is to provide an apparatus and method for determining the zero line reference which is accurate, reliable and economical.

Other objects will be in part obvious and in part pointed out more in detail hereinafter.

Accordingly, the foregoing and related objects and advantages may be obtained in a method for determining the zero line reference is an atomic absorption spectrophotometer of the type having an atomizer and burner for atomizing a sample with a flame receiving a regulated or fixed flow of oxidizing agent comprising the steps of halting the flow of sample to the flame of the burner while maintaining the fixed flow of oxidizing agent to the flame and measuring the light absorption of the flame without sample to define a zero line reference. The flow oxidizing agent to the atomizer is halted to stop the flow of sample to the flame and the supply of oxidizing agent to the burner is increased to compensate for the stoppage of oxidizing agent to the flame via the atomizer. In one embodiment of the invention, the flow of oxidizing agent to the atomizer is selectively by-passed to the flame.

An atomic absorption spectrometer apparatus of the present invention includes a burner for producing a flame for burning a sample for atomic absorption spectrometry. A first regulated supply provides a regulated flow of fuel gas and oxidizing agent to the burner for producing the flame. An atomizer introduces sample to the flame in an aerosol form and is connected to a second regulated supply for providing a regulated flow of oxidizing agent to the atomizer during a sample analysis operation. A flow meter measures the flow of oxidizing agent to the atomizer. A light source generates a measuring light beam and the detector produces a measuring signal based upon the absorption of the measuring light beam in the flame. A valve assembly is connected to the atomizer oxidizing agent supply for selectively halting the flow of oxidizing agent to the atomizer and providing an additional flow of oxidizing agent to the burner during a measurement correction determination operation. A regulator controls the additional flow of oxidizing agent to the burner so that the additional flow is equal to the flow of oxidizing agent to the atomizer during a sample analysis operation. An electronic circuit defines the absorption of the measuring beam during a measurement correction determination operation as the zero line measurement.

DESCRIPTION OF THE PREFERRED EMBODIMENT

Figure 1:
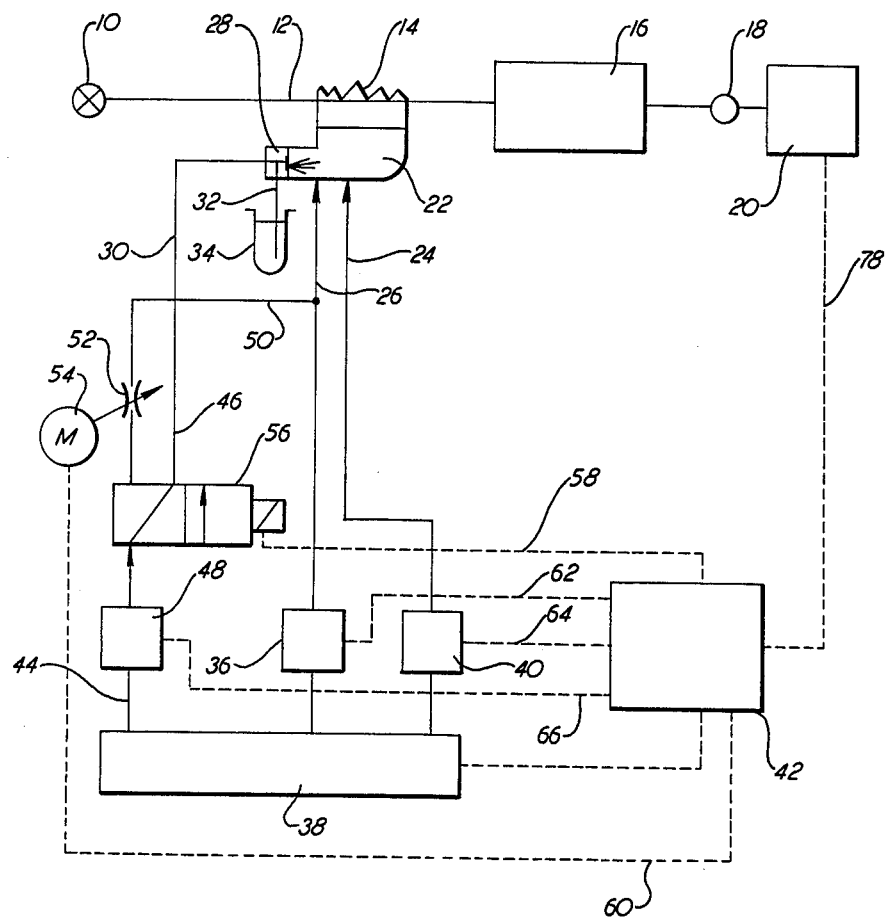
FIG. 1 is a schematic diagram of an atomic absorption spectrometer according to the present invention.

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the light source 10 generates a measuring light beam 12 formed by light having a line spectrum which corresponds to the resonance lines of the looked-for element. The measuring light beam 12 passes through a flame 14 and a monochromator 16 and impinges upon a photoelectric detector 18 to generate a signal which is processed in a signal processing circuit 20. This is a conventional configuration for an atomic absorption spectrometer which operates using a flame.

The flame 14 burns at the burner 22 which is supplied with a fuel gas such as acetylene through a connector 24. The burner 22 is also supplied with an oxidizing agent such as air or laughing gas through a connector 26. The fuel gas and oxidizing agent are mixed in a mixing chamber of the burner 22 and fed to the flame 14. An atomizer 28 is provided at the burner 22 and is supplied with oxidizing agent through a connector 30.

During normal measuring operation, the atomizer 28 takes in sample liquid from a sample vessel 34 through a conduit 32. The sample liquid is entrained by the flow of oxidizing agent and a major portion thereof is sprayed into the mixing chamber as a fine aerosol and is entrained and fed into the flame 14 by the flow of fuel gas and oxidizing agent. The components of the sample liquid are decomposed and atomized in the flame such that the different elements contained in the sample form a cloud of atoms in which the elements are present in the atomic state. The desired element has resonance lines corresponding to the line spectrum of the measuring light beam 12 and absorbs the light of the measuring light beam. The measuring light beam 12 is thereby attenuated by the flame 14 according to the amount of the desired element in the flame 14. An absorption signal indicative of the concentration of the desired element in the sample is generated by the detector 18.

A flow meter 36 measures the flow of oxidizing agent supplied to the burner 22 by means to be described for regulated fuel gas and oxidizing agent supply and generally designated by the numeral 38 in FIG. 1. A flow meter 40 measures the flow of fuel gas supplied to the burner 22 through the connector 24. The flow meters 36 and 40 supply signals to a microprocessor controlled electronic circuit 42.

The atomizer 28 receives oxidizing agent via conduits 44, 46 from the oxidizing agent supply means which is part of said means 38 for regulated fuel gas and oxidizing agent supply. The flow of oxidizing agent is directed to the atomizer 28 and effects the take-in and atomizing of the sample liquid in the described manner. A flow meter 48 is positioned in the conduit 44 for measuring the flow of oxidizing agent supplied to the atomizer 28. A conduit 50 is connected to the connector 26 of the burner 22 and contains an adjustable flow restrictor 52 in the form of a needle valve. The adjustable flow restrictor 52 is adjustable by means of a servomotor 54.

A switching valve 56 provides a connection between the conduits 44 and 46 in a first switched position as illustrated in FIG. 1 and a connection between the conduits 44 and 50 in a second switched position. The switching valve 56 is controllable by means of the electronic circuit 42 as indicated by the broken line 58. The servomotor 54 is also controlled by the electronic circuit 42 as indicated by the broken line 60. The flow meters 36, 40 and 48 supply measured flow value signals to the electronic circuit 42 as indicated by the respective broken lines 62, 64 and 66.

In the illustrated first switched position of the switching valve 56, the regulated flow of oxidizing agent is supplied to the atomizer 28 through conduit 44 and conduit 46 for nebulization and atomization of the sample liquid in the flame 14 for measurement of the atomic absorption of the sample. The zero line reference measurement is made with the switching valve 56 in the second position.

When switching the switching valve 56 to the second switched position, the flow of oxidizing agent supplied to the atomizer is interrupted. The burner 22 is supplied with an additional flow of oxidizing agent through conduit 50 by-passing the atomizer 28. This additional flow is as strong as the flow of oxidizing agent to the atomizer 28 measured during operation of the atomizer 28. Therefore, the total amount of oxidizing agent supplied to the burner 22 remains unchanged so that the flame 14 burns essentially unchanged in the regard. Rather, there is merely no sample liquid passed into the flame 14. The resulting absorption of the measuring light beam 12 thus defines the zero line reference. The conduit 50 represents a by-pass of the atomizer 28 by which an additional flow of oxidizing agent can be directly supplied to the burner. The switching valve 56 provides switching means for switching the flow of oxidizing agent supplied to the atomizer 28 to the by-pass conduit 50. The servomotor 54 and the adjustable flow restrictor 52 form the actuator of regulating means for regulating the flow of oxidizing agent. The flow rate of oxidizing agent to the burner 22 through the by-pass conduit 50 is adjusted by means of the servomotor 54 and the flow restrictor 52 to be equal to the flow rate to the atomizer 28 during sample measurement.

Figure 2:
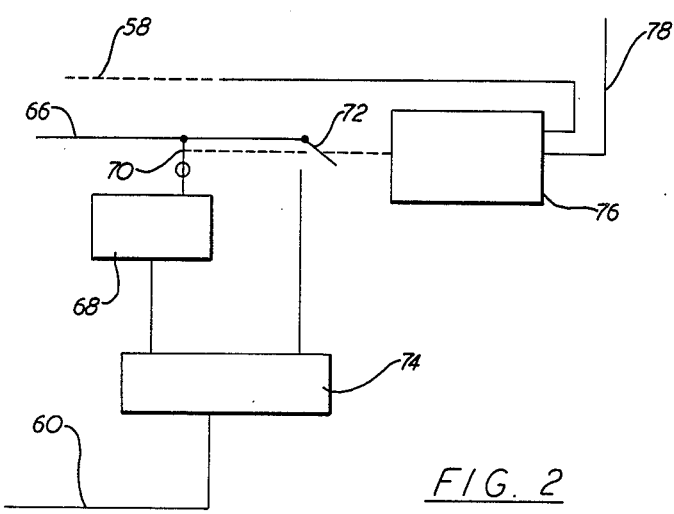
FIG. 2 is an enlarged schematic diagram of the gas regulating means for the fuel gas and oxidizing agent supply to the burner in the atomic absorption spectrometer of FIG. 1.

As evident from FIG. 2, the means for regulating the additional flow of oxidizing agent to the burner 22 in the zero line reference measurement mode comprises a memory 68 for storing the value of the flow supplied to the atomizer and measured by the flow meter 48 during operation of the atomizer as well as means for measuring the flow conducted from the oxidizing agent supply means through the switching valve 56 to the by-pass conduit 50. Such measuring means are formed in this apparatus by the same flow meter 48 which is arranged between the oxidizing agent supply means and the switching valve 56. As indicated in FIG. 2, the signal line is connectable with the memory 38 which is symbolically indicated by an actuator 70. In the second switched state, the signal line 66, as indicated by the actuator 72, is directly connected to regulating means 74. The regulating means 74 compares the flow of oxidizing agent conducted through the by-pass conduit 50 and measured by the flow meter 48 with the stored value in memory 68 which corresponds to the flow of oxidizing agent to the atomizer 28 during the sample measuring operation. The comparator 74 controls the servomotor 54 through the connection 60. The servomotor 54 adjusts the adjustable flow restrictor 52 with the servomotor 54 being controlled by the regulating means 74 in the sense of equalizing the flow through the by-pass conduit 50 to the stored value in the memory 68. The switching of the "actuators" 70 and 72 is effected by means of a control 76 which simultaneously controls the switching valve 56 through the connection 58 and supplies a signal to the signal processing circuit 20 through a connection 78. The memory 68, the regulating means 74 and the control 76 form part of the microprocessor controlled electronic circuit 42 shown in FIG. 1.

Figure 3:
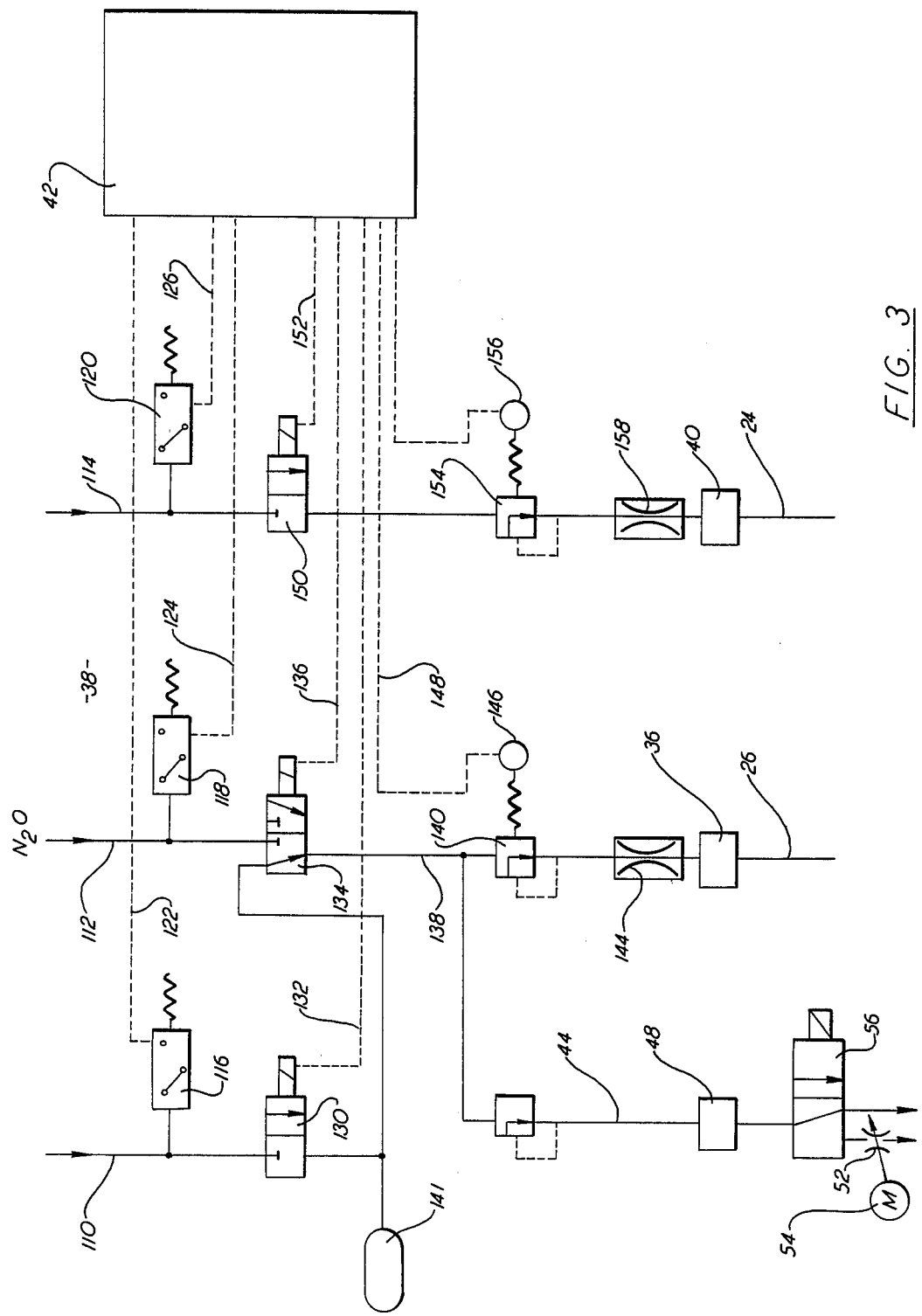
FIG. 3 is a block diagram of the means for regulated fuel gas and oxidizing agent supply.

FIG. 3 shows details of the means for regulated fuel gas and oxidizing agent supply. The gas regulating means comprises a first connector 110 to which a first oxidizing agent in the form of compressed air is connectable, a second connector 112 connectable to a source of laughing gas as a second oxidizing agent and a third connector 114 connectable to a source of fuel gas, preferably acetylene. Each of the three connectors 110, 112 and 114 is connected to a respective pressure sensor 116, 118 and 120. The pressure sensors 116, 118, 120 signal the presence of gas pressure at the respective connections. These signals are applied to the microprocessor controlled electronic circuit 42 via respective signal lines 122, 124 and 126.

A solenoid shut-off valve 130 is connected to the first connector 110 and controlled via a control line 132 by the electronic circuit 42. The shut-off valve 130 is shut off in the absence of current. A 3/2-directional control valve 134 is constructed as a solenoid valve and controlled via a control line 136 by the electronic circuit 42. In its first switched position, the 3/2-directional control valve connects the first connector 110 and the shut-off valve 130 with a conduit 138 and the second connector 112 is shut off. In its second switched position, the 3/2-directional control valve 134 connects the second connector 112 with the conduit 138 whereas the connection to the shut-off valve 130 and the first connector 110 are shut off. In the absence of current flow, the 3/2-directional control valve is in its first switched position as illustrated in FIG. 3.

A branch conduit 44 leads from the conduit 138 to the atomizer. A reservoir 141 is connected between the shut-off valve 130 and the 3/2-directional control valve 134. The conduit 138 leads to a pressure regulator 140. The output of the pressure regulator 140 is connected through a fixed flow restrictor 144 to the oxidizing agent connector 26 of the burner 22. The pressure regulator 140 constitutes a standard pressure reducing valve having a reference value which is variable by means of an adjusting spindle. The adjusting spindle is adjustable by means of a servomotor 146. The servomotor 146 or appropriate pick-off means transmit position signals to the electronic circuit 42. The servomotor 146 is correspondingly controlled by the electronic circuit 42. This is indicated by the connection 148 shown in broken lines.

A solenoid shut-off valve 150 is connected after the third connector 114. The shut-off valve 150 is controlled via a connection 152 by the electronic circuit 42. The third connector 114 is connected to a pressure regulator 154 through the shut-off valve 150. The pressure regulator 154 also constitutes a standard pressure reducing valve like the pressure regulator 140. An adjusting spindle of the pressure regulator 154 for adjusting the reference value is adjustable by means of a servomotor 156. The servomotor 156 or appropriate pick-off means transmits position signals to the electronic circuit 42 and is correspondingly controlled by the electronic circuit 42. The output of the pressure regulator 154 is connected to the fuel gas connection 24 of the burner 22 through a fixed flow restrictor 158.

This arrangement substantially corresponds to the arrangement according to the not prepublished German Patent Application No. P 34 07 552.6 incorporated by reference herein and operates substantially in the same manner as this arrangement. Reproducably defined flows of oxidizing agent and fuel gas, respectively, can be adjusted by means of the pressure regulator 140 and 154 which are adjustable in a defined manner, in combination with the fixed flow restrictors 144 and 158, respectively. The 3/2-directional control valve 134 allows changing-over from air as the oxidizing agent to laughing gas. The pressure sensors 116, 118 and 120 ensure that the required gas pressure is present. The control is effected by the electronic circuit 42 to the program described in the aforementioned patent application. The flow meter 48 is located in the conduit 44. The flow meters 36 and 40 are respectively connected to follow the flow restrictors 144 and 148 as illustrated in FIG. 1.

As will be apparent to persons skilled in the art, various modifications and adaptations of the structure above described will become readily apparent without departure from the spirit and scope of the invention, the scope of which is defined in the appended claims.

What is claimed is:

1. A method of determining a zero line reference in an amount absorption spectrometer having an atomizer and burner for atomizing a sample with a flame receiving a regulated or fixed flow of oxidizing agent comprising the steps of
    measuring the flow rate of oxidizing agent to the atomizer during the atomization of sample in the flame,
    halting the flow of sample to the flame of the burner while maintaining the fixed flow of oxidizing agent to the flame, said steps of halting the flow of sample and maintaining the fixed flow of oxidizing agent comprising halting the flow of oxidizing agent to the atomizer to stop the flow of sample to the flame and increasing the flow of oxidizing agent to the burner by the measured flow rate, and
    measuring the light absorption of the flame without sample to define a zero line reference.

2. The method of claim 1 which comprises selectively by-passing the flow of oxidizing agent to the atomizer to the burner.

3. The method of claim 2 which comprises providing a by-pass connector to the burner and selectively diverting the flow of oxidizing agent to the atomizer with the by-pass connector so as to conduct said flow to the burner.

4. An atomic absorption spectrometer comprising
    burner means for producing a flame for burning a sample for atomic absorption spectrometry,
    first means for providing a regulated flow of fuel gas and oxidizing agent to said burner means for producing a flame, atomizer means for introducing sample to the flame of said burner means in an aerosol form, second means for providing a regulated flow of oxidizing agent to said atomizer means during a sample analysis operation, means for measuring the flow of oxidizing agent to said atomizer means, means for generating a measuring light beam, detector means for providing a measuring signal based upon absorption of the measuring beam in the flame of said burner means, means for selectively halting the flow of oxidizing agent to the atomizer means during a measurement correction determination operation, third means for selectively providing an additional flow of oxidizing agent to said burner means during a measurement correction determination operation, said third means having means for regulating said additional flow to equal the flow of oxidizing agent to said atomizer means during the sample analysis operation, and means for defining the absorption of the measuring beam in the flame during a measurement correction determination operation as the zero line reference.

5. The device of claim 4 wherein said third means for selectively providing an additional flow of oxidizing agent comprises a by-pass conduit interconnecting said burner means and said second means for providing a regulated flow to said atomizer means so as to by-pass said atomizer means.

6. The device of claim 5 wherein said means for selectively halting the flow of oxidizing agent to said atomizer means comprises valve means actuable between first and second positions with said valve means diverting oxidizing agent from said second means for providing a regulated flow into said by-pass conduit in said first position and passing oxidizing agent to said atomizer means in said second position.

7. The device of claim 5 wherein said means for regulating said additional flow comprises means for storing the measurement of flow of oxidizing agent to said atomizer means during a sample analysis operation, means for measuring the flow of oxidizing agent through said by-pass conduit during a measurement correction determination operation, regulating means for comparing said measurement of flow of oxidizing agent to said atomizer to the flow of oxidizing agent through said by-pass conduit, and flow restrictor means for controlling the flow through said by-pass conduit, said flow restrictor means being connected to said regulating means so as to control the flow of oxidizing agent through said by-pass conduit to equal the flow of oxidizing agent to said atomizer means during a sample analysis operation.

* * * * *

UNITED STATES PATENT AND TRADEMARK OFFICE
CERTIFICATE OF CORRECTION

PATENT NO. : 4,773,755
DATED : September 27, 1988
INVENTOR(S) : Bernhard Huber

It is certified that error appears in the above-identified patent and that said Letters Patent is hereby corrected as shown below:

Column 6, line 37, change "amount" to --atomic--.

Signed and Sealed this

Sixth Day of June, 1989

Attest:

DONALD J. QUIGG

Attesting Officer

Commissioner of Patents and Trademarks